United States Patent [19]

Avitall

[11] Patent Number: 5,454,370
[45] Date of Patent: Oct. 3, 1995

[54] MAPPING AND ABLATION ELECTRODE CONFIGURATION

[76] Inventor: Boaz Avitall, 4868 N. Ardmore Ave., Milwaukee, Wis. 53217

[21] Appl. No.: 161,916

[22] Filed: Dec. 3, 1993

[51] Int. Cl.⁶ ....................................................... A61B 5/04
[52] U.S. Cl. .............................. 128/642; 607/98; 607/99; 607/122
[58] Field of Search ............................ 128/642; 607/122, 607/125, 126, 98, 99

[56] References Cited

U.S. PATENT DOCUMENTS

| | | | |
|---|---|---|---|
| 4,633,880 | 1/1987 | Osypk et al. | 128/642 |
| 4,699,147 | 10/1987 | Chilson et al. | 128/642 |
| 4,777,955 | 10/1988 | Brayton et al. | |
| 4,785,815 | 11/1981 | Cohen. | |
| 5,044,375 | 9/1991 | Bach, Jr. et al. | |
| 5,228,442 | 7/1993 | Imran | 128/642 |
| 5,263,493 | 11/1993 | Avitall. | |
| 5,275,162 | 1/1994 | Edwards | 607/122 |
| 5,279,299 | 1/1994 | Imran | 128/642 |
| 5,318,525 | 6/1994 | West et al. | 607/122 X |
| 5,327,905 | 7/1994 | Auitall | 128/642 X |

OTHER PUBLICATIONS

Avitall, Boaz, et al., "Physics and Engineering of Transcatheter Cardiac Tissue Ablation", JACC, vol. 22, No. 3, Sept. 1993, pp. 921–932.

Langberg, Jonathan J., et al., "Temperature–Guided–Radio–frequency Catheter Ablation with Very Large Distal Electrodes", Circulation, vol. 88, No. 1, Jul. 1993, pp. 245–249.

*Primary Examiner*—Lee S. Cohen
*Assistant Examiner*—Brian L. Casler
*Attorney, Agent, or Firm*—Haugen and Nikolai

[57] ABSTRACT

A mapping and ablation distal vascular catheter arrangement is disclosed which is suitable for association with a vascular catheter system and which includes a segmented mapping/ablation electrode system in which the lesion size including length, width and depth is made flexible and the ability to discretely map localized electrical activity using the same is preserved. The electrode system includes a plurality of serially spaced individual electrodes on the surface of a distal working catheter area which can be utilized together to produce the effect of an elongated segmented ablation electrode or individually utilized to map local electrical activity. A control system or device is provided that allows the individual electrodes to be connected to one or more receiving/recording/display devices in any desired pattern. That is, recording or mapping may be conducted using any configuration of electrodes for receiving signals. This allows signals or propagated wavefronts to be detected between the most likely electrodes, i.e., the tissue of interest to be used. The control system further permits ganging of the electrodes in any manner when connected to a source of RF ablation energy.

18 Claims, 1 Drawing Sheet

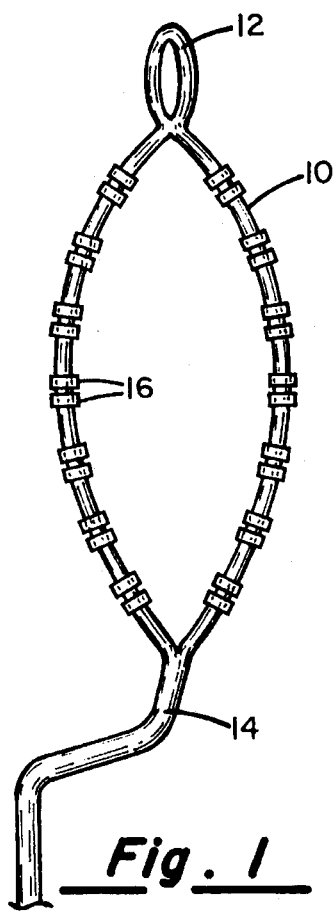
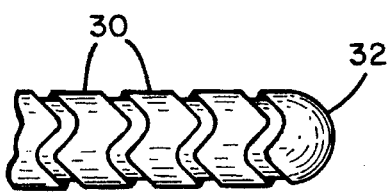
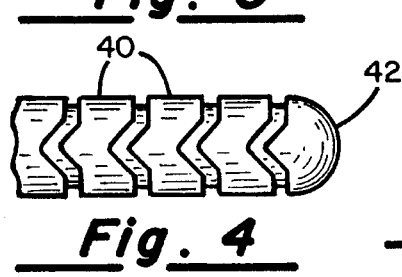
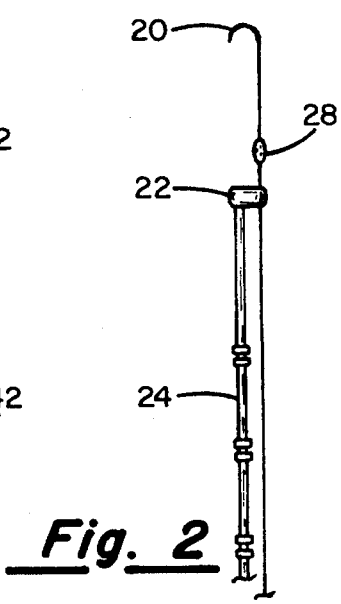
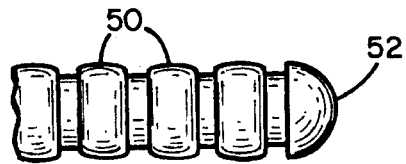
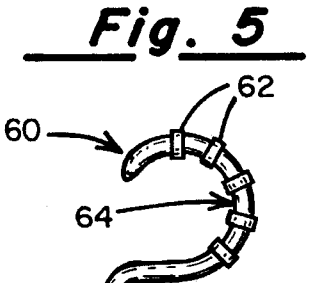
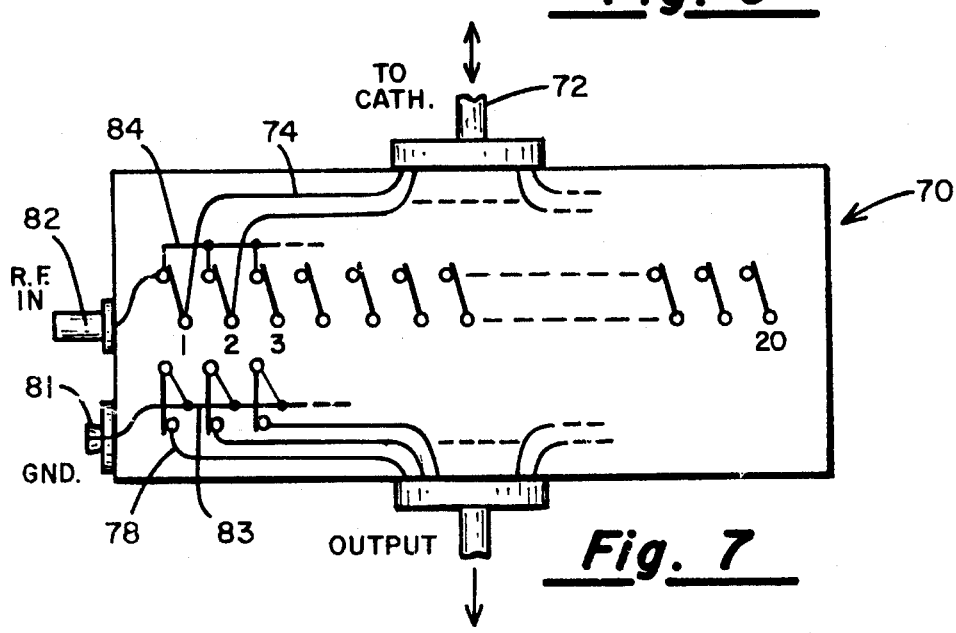

MAPPING AND ABLATION ELECTRODE CONFIGURATION

BACKGROUND OF THE INVENTION

I. Field of the Invention

The present invention relates generally to the field of receiving and recording signals indicative of or inducing cardiac activity (mapping) and transmitting electric energy or radio frequency (RF) power to tissue surfaces (ablating) using steerable vascular cardiac catheters. The invention is particularly directed to a mapping and ablation catheter electrode system which can precisely locate localized cardiac electrical activity signals regardless of the direction of the propagation wavefront and yet create linear continuous lesions of significant size.

II. Discussion of the Related Art

Steerable catheter systems of several types have been devised. Such devices can be inserted into blood vessels or similar bodily areas and their distal ends navigated through the tortuous vascular path to reach areas of the body normally inaccessible without surgery. Catheters of the steerable or self-navigating type, having distal electroded sections for monitoring parts of the body, such as for electrically mapping the heart by receiving and transmitting electrical signals related to the operation of that organ to recording signal processing and display devices are also known. The ability to successfully record impulses or signals and from them electrically map the cardiac chambers and valves using flexible catheters having steerable electroded tips has further led to the use of the technique of transcatheter ablation of cardiac tissues that have been identified as the cause of cardiac arrhythmias. This technique has emerged as one of the most important advances in cardiac electrophysiology. Its goal is to destroy the arrhythmogenic tissue without compromising the mechanical or muscular integrity of the cardiac tissues and vessels.

Not long ago, for example, many patients with Wolff-Parkinson-White syndrome or ventricular tachycardia underwent surgical dissection of the arrhythmogenic tissue followed by a painful and prolonged recovery. Introduction of the transcatheter approach has dramatically reduced the suffering and cost of this definitive treatment for many causes of cardiac arrhythmias.

The general approach to this procedure initially preferably utilized high energy direct current delivered to the catheter poles, for example, to disrupt the A-V node condition and even to create a complete heart block by ablating the His bundle. The diffuse nature of direct current energy tissue injury, the relatively high rate of serious complications and the limited ability of the operator to control the energy delivered have limited the usefulness of this approach and have led to the development of approaches using alternative energy sources. As a result, more recently, radio frequency (RF) has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", *JACC* Volume 22, No. 3:921-32. The rapid clinical acceptance of this procedure and the proliferation of physicians engaged in transcatheter tissue ablation has mandated the development of improved steerable catheter devices with more sophisticated electrode configurations.

In order to produce large, rather deep lesions to ablate certain arrhythmias, particularly those associated with ventricular tachycardia due to reentry in patients with a history of heart attacks, or to produce longer linear lesions, the trend has been to employ longer or very large distal tip electrodes requiring rather high RF power for use with RF ablation. Electrodes up to 12 mm long are described by Langberg et al, for example, "Temperature-Guided Radio Frequency Catheter Ablation with Very Large Distal Electrodes" in *Circulation*, Vol. 88, No 1, Jul. 1993 (pp. 245–249). This approach is typical of the current trend. While such large electrodes are useful for increasing lesion size and ablating tissue, this is not achieved without compromising the ability to discretely map localized electrical activity. Thus, there remains a definite need for the provision of an electrode system which not only enables the production of any desired size lesion, but also enables the operator to maintain accurate localized mapping ability using the same electrodes.

Accordingly, it is a primary object of the present invention to provide an improved mapping/ablation electrode arrangement which provides for flexible lesion size yet maintains discrete localized mapping ability.

Another object of the present invention is the provision of a segmented ablation/mapping multi-electrode system that maintains the ability to map localized electrical activity irrespective of directionality of the propagating wavefront.

Yet another object of the invention is the provision of a segmented or multi-electrode mapping/ablation system that enables the operator to adjust the lesion size (width, length and depth).

Other objects and advantages of the invention will occur to those skilled in the art in accordance with the following description, specification and drawings.

SUMMARY OF THE INVENTION

The present invention provides a mapping and ablation distal vascular catheter arrangement suitable for association with a vascular catheter system and which includes a segmented mapping/ablation electrode system in which the lesion size including length, width and depth is made flexible and the ability to discretely map localized electrical activity using the same is preserved. The electrode system includes a plurality of serially spaced individual electrodes on the surface of a distal working catheter area which can be utilized together to produce the effect of an elongated segmented ablation electrode or individually utilized to map local electrical activity. A control system or device is provided that allows the individual electrodes to be connected to one or more receiving/recording/display devices in any desired pattern. That is, recording or mapping may be conducted using any configuration of electrodes for receiving signals. This allows signals or propagated wavefronts to be detected between the most likely electrodes, i.e., the tissue of interest to be used. The control system further permits ganging of the electrodes in any manner when connected to a source of RF ablation energy.

One embodiment of the invention contemplates a distal working electrode area including two or more spaced ring electrodes connected to individual insulated input/output conductors and having a length of approximately 1–3 mm and an inter-electrode space of from 0.5 to 2.0 mm. The preferred spacing is from 0.5 to 1.0 mm. The typical diameter of the working catheter area is approximately 5 F to 10 F. Where appropriate to the catheter design, a tip electrode may also be used. Other electrode configurations include spaced radially overlapping electrodes which utilize a chevron pattern or a yin-yang pattern such that the electrodes of the system not only can be ganged together for producing larger or longer continuous ablation but also individually can be used to map localized electrical activity in a manner which prevents localized signals from being missed and allows detection of activation wavefronts that are transversing the recording electrodes in any direction.

These electrode configurations provide the operator with the flexibility to achieve the most accurate mapping available yet and to increase lesion size as desired. The control system of the invention can be used with any electrode configuration.

BRIEF DESCRIPTION OF THE DRAWINGS

In the drawings, wherein like numerals are utilized to designate like parts throughout the same:

FIGS. 1–6 are fragmentary schematic representations of a variety of mapping/ablation working catheter tip areas showing various electrode configurations; and FIG. 7 is a schematic control system diagram showing mapping/recording and ablation connections for multiple electrode systems such those illustrated in FIGS. 1–6.

DETAILED DESCRIPTION

In accordance with the FIGS. 1–6, there are a variety of electrode configurations employing a plurality of spaced electrodes which can be used for mapping and/or ablating cardiac tissue in various chambers and locations. The loop system of FIG. 1 includes a main loop form 10, which may be preformed or adjustable in shape, having a tail extension 12 to assist in anchoring the loop as over the tricuspid valve or the like and which is part of a distal working catheter area including a shaped transition section 14. The electrode array includes individual electrodes 16 which are illustrated as being generally arranged in pairs. Typically, such electrodes are ring electrodes which may have one or more flattened surfaces, as desired for the particular cardiac area to be addressed. They are typically about 1.0 to 3.0 mm in length and separated by a distance 0.5–1.0 mm arranged in pairs spaced up to approximately 8 mm apart. FIG. 2 depicts a similar paired electrode arrangement on another type of distal working catheter embodiment which includes a guidewire 20 on which is slidably mounted a distal catheter rider 22 which, in turn, is connected to the distal catheter segment 24 and which can be used with a more proximal control element (not shown) in conjunction with a distal stop member which limits the distal movement of the rider 22 as shown at 28 to shape the distal catheter 24 into a ring or other shape. This system is particularly useful in addressing the right atrium via either vena cava. The electrode configuration includes pairs of electrodes 26 which may be arranged as in the loop of FIG. 1 with regard to size and spacing.

FIGS. 3 and 4 depict other serially spaced electrode arrangements in which the electrodes, although spaced longitudinally apart, overlap radially in one or more places such that signals such as activation wavefronts received from localized electrical activity which may not be between spaced activated electrodes or pairs of electrodes in the other embodiments will not be missed and regardless of transversing direction will be picked up between two more of the electrodes. Thus, in FIG. 3, there is shown a yin-yang pattern utilizing longitudinally spaced electrodes 30 with tip electrode 32. These electrodes, like the other previously described, may be ring electrodes generally 1–3 mm in length and spaced apart 0.5–1.0 mm such that overlapping takes place in the yin-yang pattern. FIG. 4 is an overlapping arrangement similar to FIG. 3 in which a pattern of serially placed spaced electrodes 40 with tip electrode 42 are given a substantially chevron pattern such that radial overlapping does occur for precision in mapping and creating overlapping lesions. The arrangement of FIG. 5 shows a plurality of closely spaced ring electrodes 50 with tip electrode 52. Although these electrodes do not radially overlap, the distance between the electrodes, typically 0.5 mm or less for 2 mm electrodes, results in the fact that few local electrical signals indicative of activity are missed and the close proximity of the electrodes creates overlapping lesions.

FIG. 6 depicts what is commonly known as a "pigtail" arrangement in which a short hook-shaped distal working catheter 60 is provided with a series of spaced ring electrodes 62 equidistant about the general curvature of the hook. The size and spacing of these electrodes also is a matter of choice, keeping in mind that the electrodes must be kept separated about the inner curvature of the working catheter area. However, an array containing 6–8 electrodes about 2 mm long separated by a distance of 0.5 to 1.0 mm provides discrete mapping and flexible lesion size.

FIG. 7 shows generally at 70 a control device for operating the electrodes of any of the system as represented in FIGS. 1–6. Each of the electrodes associated with any of the distal working catheter systems utilized for mapping and ablation is provided with its own separately insulated electrical lead. These leads are threaded through catheter or sheath lumens in a well-known manner and are connected to outside recording/control means as by a jack connected to a flexible wiring harness in a well-known manner, such as shown in applicant's application Ser. No. 07/989,804, filed Dec. 11, 1992, now U.S. Pat. No. 5,327,905, issued Jul. 12, 1994, the details of which, to the extent necessary, are deemed incorporated herein by reference.

The connection of the multiple wires or wiring harness with the control system is shown schematically by a plug at 72, where each of the conductors as at 74 is associated with a switch as at 76. The switches are connected in a manner such that each can separately be connected to a recording/display output via a conductor such as 78 collectively connected as by multiple connector or plug system 80. A suitable isolating ground shield is used in a well-known manner as indicated at 81. The use of the ground switch 83 assures that, when any of the catheter electrodes are connected to the RF generator input 82, the recording inputs as at 78 are connected to ground shield 81 to minimize RF interference with the recording devices. Conversely, switch 83 is opened during mapping.

The system allows separate signals to be picked up by each of the serially placed electrodes such that localized electrical activity is mapped as to the electrode involved, and the location of that electrode can also be noted. A separate source of radio frequency energy is connected at 82 in a manner such that it will not interfere with the recording or display devices but can be connected to one or more of the serially spaced electrodes such that they be utilized in any single or multiple electrode ablating arrangement desired. This is indicated at 84.

Enlarging the size of an ablation electrode will result in a larger lesion by increasing electrode/tissue contact if the amount of radio frequency power is proportionately increased. The versatile and beneficial effect of the use of a plurality of spaced electrodes in accordance with the invention has also been demonstrated.

In one embodiment of the present invention, such as that shown in FIG. 5, a 2 mm tip electrode followed by three 2 mm ring electrodes spaced 0.5 mm apart were mounted in a 7 F deflectable catheter. In five models, the electrodes were placed in the epicardial free wall of the right ventricle. The electrode-tissue contact was fixed and intracardiac recordings using the close-spaced 2 mm electrodes yielded sharp and discrete high frequency content electrograms. Radio frequency lesions were created using 60 watts of power applied to several electrode combinations: the 2 mm tip electrode plus the first ring electrode (2+2), the tip electrode plus the first and second ring electrodes (2+2+2) and the tip electrode plus all three ring electrodes (2+2+2+2). These combinations were compared with lesions created in a standard 4 mm electrode as shown in Table I below.

|  | Lesion Size (mm) | | | |
| --- | --- | --- | --- | --- |
|  | 2 + 2 | 2 + 2 + 2 | 2 + 2 + 2 + 2 | 4 mm |
| LENGTH | 11.4 ± 1.6 | 11.9 ± 0.9* | 12.3 ± 0.7* | 9.1 ± 0.4 |
| WIDTH | 7.8 ± 1.1# | 6.5 ± 1.1 | 5.4 ± 0.2 | 6.9 ± 1.2 |
| DEPTH | 7.1 ± 1.4* | 7.1 ± 1.2* | 6.8 ± 1.3 | 5.3 ± 0.6 |

*$p < 0.05$ vs 4 mm, #$p < 0.05$ vs. 2 + 2 + 2 + 2

As can be seen from the Table, segmented ablation electrode configurations 2+2 and 2+2+2 result in a significantly greater lesion depth than the standard 4 mm electrode. The length is also significantly increased even using just the 2+2 system. It should be noted that the paired ring electrodes as shown in FIGS. 1 and 2 actually in effect are the same as having multiple sets of 2+2 electrode configurations available in a longer distal working catheter area.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A vascular cardiac mapping and ablation catheter comprising:
   (a) a main catheter or sheath having a distal portion and a flexible catheter section disposed at said distal portion of said main catheter or sheath having a distal catheter working area;
   (b) a plurality of spaced-apart ring electrodes carried by said distal catheter working area, wherein the electrodes overlap radially in a plane perpendicular to a central axis of said distal catheter working area and a plurality of electrical conductors, one associated with each of said electrodes;
   (c) switching means for selectively, conductively connecting said electrodes via said electrical conductors to mapping recording equipment and an electrical energy source, said switching means having connectors for attaching to the mapping recording equipment and the electrical energy source.

2. The catheter of claim 1, wherein said plurality of spaced apart electrodes overlap in a chevron design.

3. The catheter of claim 2 wherein the plurality of spaced-apart electrodes are about 1–3 mm in length and separated by an inter-electrode space of about 0.5 to 1.0 mm.

4. The catheter of claim 1, wherein said plurality of spaced apart electrodes overlap in a yin-yang design.

5. The catheter of claim 4 wherein the plurality of spaced-apart electrodes are about 1–3 mm in length and separated by an inter-electrode space of about 0.5 to 1.0 mm.

6. The catheter of claim 1 wherein the plurality of spaced-apart electrodes are less than about 4 mm in length and separated by an inter-electrode space of about 0.5 to 1.0 mm.

7. The catheter of claim 6 wherein the number of spaced-apart electrodes is from two to six.

8. A vascular cardiac mapping and ablation catheter, comprising:
   (a) a main catheter or sheath having a distal portion and flexible catheter section disposed at said distal portion of said main catheter or sheath and having a distal catheter working area;
   (b) a plurality of spaced-apart radially overlapping ring electrodes carried by said distal catheter working area and including a distal tip electrode and a plurality of electrical conductors, one associated with each of said electrodes; and
   (c) switching means for selectively, conductively connecting said electrodes via said electrical conductors to mapping recording equipment and an electrical energy source, said switching means having connectors for attaching to the mapping recording equipment and the electrical energy source.

9. The catheter of claim 8, wherein said plurality of spaced-apart electrodes are ring electrodes that overlap in a chevron design.

10. The catheter of claim 9 wherein the plurality of spaced-apart electrodes are about 1–3 mm in length and separated by an inter-electrode space of about 0.5 to 1.0 mm.

11. The catheter of claim 8, wherein said plurality of spaced-apart electrodes are ring electrodes that overlap in a yin-yang design.

12. The catheter of claim 11 wherein the plurality of spaced-apart electrodes are about 1–3 mm in length and separated by an inter-electrode space of about 0.5 to 1.0 mm.

13. The catheter of claim 8, wherein the plurality of spaced-apart electrodes are less than 4 mm in length and separated by an inter-electrode space of about 0.5 to 1.0 mm.

14. The catheter of claim 13 wherein, the plurality of spaced-apart electrodes includes from two to six of said electrodes.

15. A method of mapping and ablating cardiac chamber surfaces comprising the steps of:
   (a) introducing a vascular cardiac mapping and ablation catheter into a cardiac chamber of interest, said catheter comprising:
      (1) a main catheter or sheath having a distal portion and a single member flexible catheter section disposed at said distal portion of said main catheter or sheath having a distal catheter working area;
      (2) a plurality of spaced-apart radially overlapping ring electrodes carried by said distal catheter working area, wherein the electrodes are spaced to produce continuous ablation lesions when consecutive electrodes are energized and a plurality of electrical conductors, one electrical conductor connected with each of said electrodes;
      (3) switching means for selectively, conductively connecting said electrodes via said electrical conductors to mapping recording equipment and an electrical energy source, said switching means having connectors for attaching to the mapping recording equipment and the electrical energy source; and wherein the method further includes at least one of the following:

(b) selectively connecting through said switching means said ring electrodes to said mapping recording equipment and mapping local electrical activity within the cardiac chamber; and (c) selectively connecting through said switching means said ring electrodes to said electrical energy source;

energizing said ring electrodes and ablating tissue within the cardiac chamber; wherein the ablating step comprises:

producing continuous ablation lesions when consecutive electrodes of said ring electrodes are energized.

16. The method of claim 15 further comprising the step of ganging two or more of said electrodes together during ablation to produce continuous elongated lesions in the tissue area affected according to the number of electrodes ganged.

17. A vascular cardiac mapping and ablation catheter, comprising:

(a) a main catheter or sheath having a distal portion including a distal end and a flexible catheter section disposed at said distal portion of said main catheter or sheath, having a single-member distal catheter working area;

(b) a plurality of relatively large ring radically overlapping electrodes having a length from about 1 to 4 mm and having an inter-electrode distance that is less than the length of the electrodes such that any elongated continuous lesion can be produced by energizing a plurality of consecutive electrodes spaced-apart on the distal working area; and (c) switching means for selectively, conductively connecting said electrodes to mapping recording equipment and an electrical energy source, said switching means having connectors for attaching to the mapping recording equipment and the electrical energy source.

18. The catheter of claim 17, wherein the distal catheter working area has a distal tip and a distal tip electrode and said plurality of electrodes are proximal to the distal tip electrode.

* * * * *